United States Patent
Du Bois

(10) Patent No.: US 7,049,317 B2
(45) Date of Patent: May 23, 2006

(54) CCR-3 RECEPTOR ANTAGONISTS

(75) Inventor: Daisy Joe Du Bois, Palo Alto, CA (US)

(73) Assignee: Syntex (U.S.A.) LLC, Palo Alto, CA (US)

(*) Notice: Subject to any disclaimer, the term of this patent is extended or adjusted under 35 U.S.C. 154(b) by 441 days.

(21) Appl. No.: 10/242,610

(22) Filed: Sep. 12, 2002

(65) Prior Publication Data

US 2003/0119885 A1 Jun. 26, 2003

Related U.S. Application Data

(60) Provisional application No. 60/318,992, filed on Sep. 13, 2001.

(51) Int. Cl.
- *A61K 31/44* (2006.01)
- *A61K 31/277* (2006.01)
- *C07D 473/00* (2006.01)
- *C07D 211/70* (2006.01)
- *C07D 207/08* (2006.01)

(52) U.S. Cl. ............ 514/269; 514/357; 514/428; 514/528; 514/613; 544/333; 548/567; 558/432; 564/189; 546/336

(58) Field of Classification Search ............ 514/357, 514/428, 528, 613, 269; 546/336; 548/567; 558/432; 564/189; 544/333
See application file for complete search history.

(56) References Cited

U.S. PATENT DOCUMENTS

| | | | |
|---|---|---|---|
| 4,098,904 A | 7/1978 | Szmuszkovicz | 514/617 |
| 4,204,003 A | 5/1980 | Szmuszkovicz | 514/599 |
| 6,166,015 A | 12/2000 | Rogers et al. | 514/243 |
| 6,462,076 B1 * | 10/2002 | Gabriel et al. | 514/463 |
| 6,576,792 B1 * | 6/2003 | Kim | 564/191 |
| 6,706,712 B1 * | 3/2004 | Cherney | 514/238.2 |

FOREIGN PATENT DOCUMENTS

| | | |
|---|---|---|
| DE | 4326344 A1 | 2/1995 |
| FR | 2729140 A1 | 7/1996 |
| WO | WO 94/20062 A2 | 9/1994 |
| WO | WO 99/64394 A1 | 12/1999 |

OTHER PUBLICATIONS

Kertesz, et al., "2,4-Substituted Pyrrolidine Derivatives—CCR-3 Receptor Antagonists". Regular U.S. Appl. No. 10/034,034, filed Dec. 19, 2001 (priority claim: U.S. Appl. No. 60/256,585, filed Dec. 19, 2000).

* cited by examiner

*Primary Examiner*—James O. Wilson
*Assistant Examiner*—Tamthom N. Truong
(74) *Attorney, Agent, or Firm*—Grant D. Green

(57) ABSTRACT

The invention provides compounds of Formula (I):

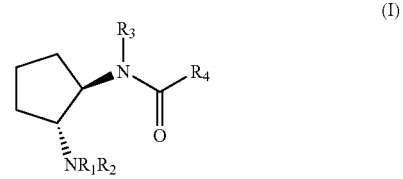

wherein $R_1$–$R_4$ have any of the values defined in the specification that are CCR-3 receptor antagonists, pharmaceutical compositions containing them, methods for their use, and methods and intermediates useful for preparing them.

13 Claims, No Drawings

CCR-3 RECEPTOR ANTAGONISTS

CROSS-REFERENCE

This application claims the benefit of priority of U.S. Provisional Patent Application Ser. No. 60/318,992, filed Sep. 13, 2001, which is incorporated herein by reference in its entirety.

FIELD OF THE INVENTION

The invention relates to certain 1,2-diaminocyclopentane derivatives that are CCR-3 receptor antagonists, pharmaceutical compositions containing them, methods for their use, and methods and intermediates useful for preparing them.

BACKGROUND INFORMATION

Tissue eosinophilia is a feature of a number of pathological conditions such as asthma, rhinitis, eczema and parasitic infections ((see Bousquet, J. et al., N. Eng. J. Med. 323: 1033–1039 (1990) and Kay, A. B. and Corrigan, C. J., Br. Med. Bull. 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils ((see Baggiolini, M. and Dahinden, C. A., Immunol. Today. 15:127–133 (1994), Rot, A. M. et al., J. Exp. Med. 176, 1489–1495 (1992) and Ponath, P. D. et al., J. Clin. Invest., Vol. 97, #3, 604–612 (1996)). However, unlike RANTES and MCP-3 which also induce the migration of other leukocyte cell types, eotaxin is selectively chemotactic for eosinophils ((see Griffith-Johnson, D. A. et al., Biochem. Biophy. Res. Commun. 197:1167 (1993) and Jose, P. J. et al., Biochem. Biophy. Res. Commun. 207, 788 (1994)). Specific eosinophil accumulation was observed at the site of administration of eotaxin whether by intradermal or intraperitoneal injection or aerosol inhalation ((see Griffith-Johnson, D. A. et al., Biochem. Biophy. Res. Commun. 197:1167 (1993); Jose, P. J. et al., J. Exp. Med. 179, 881–887 (1994); Rothenberg, M. E. et al., J. Exp. Med. 181, 1211 (1995) and Ponath, P. D., J. Clin. Invest., Vol. 97, #3, 604–612 (1996)).

Glucocorticoids such as dexamethasone, methprednisolone and hydrocortisone have been used for treating many eosinophil-related disorders, including bronchial asthma ((R. P. Schleimer et al., Am. Rev. Respir. Dis., 141, 559 (1990)). The glucocorticoids are believed to inhibit IL-5, IL-3 mediated eosinophil survival in these diseases. However, prolonged use of glucocorticoids can lead to side effects such as glaucoma, osteoporosis and growth retardation in the patients ((see Hanania, N. A. et al., J. Allergy and Clin. Immunol., Vol. 96, 571–579 (1995) and Saha, M. T. et al., Acta Paediatrica, Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to eotaxin, RANTES and MCP-3. When transfected into a murine pre-.beta. lymphoma line, CCR-3 bound eotaxin, RANTES and MCP-3 conferred chemotactic responses on these cells to eotaxin, RANTES and MCP-3 ((see Ponath, P. D. et al., J. Exp. Med. 183, 2437–2448 (1996)). The CCR-3 receptor is expressed on the surface of eosinophils, T-cells (subtype Th-2), basophils and mast cells and is highly selective for eotaxin. Studies have shown that pretreatment of eosinophils with an anti-CCR-3 mAb completely inhibits eosinophil chemotaxis to eotaxin, RANTES and MCP-3 ((see Heath, H. et al., J. Clin. Invest., Vol. 99, #2, 178–184 (1997)). Applicants' issued U.S. patents U.S. Pat. Nos. 6,140,344 and 6,166,015 and published EP application EP903349, published Mar. 24, 1999 disclose CCR-3 antagonists that inhibit eosinophilic recruitment by chemokine such as eotaxin.

Therefore, blocking the ability of the CCR-3 receptor to bind RANTES, MCP-3 and eotaxin and thereby preventing the recruitment of eosinophils should provide for the treatment of eosinophil-mediated inflammatory diseases.

SUMMARY OF THE INVENTION

The present invention concerns novel 1,2-diaminocyclopentane derivatives which are capable of inhibiting the binding of eotaxin to the CCR-3 receptor and thereby provide a means of combating eosinophil induced diseases, such as asthma.

In a first aspect, this invention provides a compound of Formula (I):

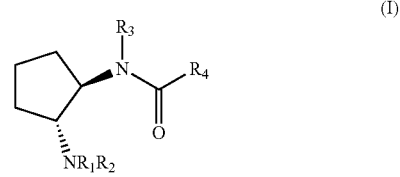

wherein:
  $R_1$ is hydrogen or alkyl;
  $R_2$ is arylalkyl;
  $R_3$ is hydrogen, alkyl, acyl, aryl, or arylalkyl;
  $R_4$ is —W—X—Y-Z;
  W is absent or alkylene;
  X is absent, carbonyl, oxy, —S(O)$_n$—, or —N($R_a$)—;
  Y is arylene or heteroarylene; and
  Z is hydrogen, aryl, heteroaryl, aryloxy, heteroaryloxy, arylalkyl, or heteroarylalkyl;
  $R_a$ is hydrogen, alkyl, acyl, aryl, arylalkyl, alkoxycarbonyl, or benzyloxycarbonyl; and
  n is 0, 1, or 2;
  or a salt thereof.

In a second aspect, this invention provides pharmaceutical compositions containing a therapeutically effective amount of a compound of Formula (I) or a pharmaceutically acceptable salt thereof, and a pharmaceutically acceptable excipient.

In a third aspect, this invention provides a method of treatment of a disease in a mammal treatable by administration of a CCR-3 receptor antagonist, comprising administration of a therapeutically effective amount of a compound of Formula (I) or a pharmaceutically acceptable salt thereof. The disease states include respiratory diseases such as asthma.

In a fourth aspect, this invention provides processes disclosed herein for preparing compounds of Formula (I).

In a fifth aspect, this invention provides novel intermediates disclosed herein that are useful for preparing compounds of Formula (I).

In a sixth aspect, this invention provides a compound of Formula (I) or a pharmaceutically acceptable salt thereof for use in medical therapy or diagnosis (e.g. for treating asthma).

In a seventh aspect, this invention provides the use of a compound of Formula (I) or a pharmaceutically acceptable salt thereof for the manufacture of a medicament useful for treating a disease in a mammal treatable by administration of a CCR-3 receptor antagonist (e.g. asthma).

DETAILED DESCRIPTION OF THE INVENTION

Definitions

Unless otherwise stated, the following terms used in the specification and claims have the meanings given below.

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl as defined herein e.g., methoxy, ethoxy, propoxy, butoxy and the like.

"Alkoxycarbonyl" means a radical —C(O)—R where R is alkoxy is as defined herein.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like. thereof.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylamino" means a radical —NHR where R represent an alkyl, cycloalkyl, or cycloalkyl-alkyl group as defined herein. Representative examples include, but are not limited to dimethylamino, methylethylamino, di(1-methylethyl) amino, (cyclohexyl)(methyl)amino, (cyclohexyl)(ethyl) amino, (cyclohexyl)(propyl)amino, (cyclohexylmethyl)(methyl)amino, (cyclohexylmethyl)(ethyl)amino, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylsulfonyl" means a radical —S(O)$_2$R where R is an alkyl, cycloalkyl or cycloalkyl-alkyl group as defined herein, e.g., methylsulfonyl, ethylsulfonyl, propylsulfonyl, butylsulfonyl, cyclohexylsulfonyl and the like.

"Alkylsulfinyl" means a radical —S(O)R where R is an alkyl, cycloalkyl or cycloalkyl-alkyl group as defined herein e.g., methylsulfinyl, ethylsulfinyl, propylsulfinyl, butylsulfinyl, cyclohexylsulfinyl and the like.

"Alkylthio" means a radical —SR where R is an alkyl as defined above e.g., methylthio, ethylthio, propylthio, butylthio, and the like.

"Aryl" means a monocyclic or bicyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and the derivatives thereof.

"Arylene" means a divalent aryl group as defined above.

"Arylalkyl" refers to an alkyl radical as defined herein in which one of the hydrogen atoms of the alkyl group is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like.

"Aryloxy" means a radical —O—R where R is an aryl group as defined herein.

"Carbamoyl" means the radical —C(=O)NH$_2$.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Cycloalkyl-alkyl" means a radical —R$^x$R$^y$ where R$^x$ is an alkylene group and R$^y$ is cycloalkyl group as defined herein, e.g., cyclohexylmethyl, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl)(methyl) amino, (cyclohexyl)(ethyl)amino, (cyclohexyl)(propyl) amino, (cyclohexylmethyl) (methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl and derivatives thereof.

"Heteroarylene" means a divalent heteroaryl group as defined above.

"Heteroarylalkyl" means an alkyl radical as defined herein in which one of the hydrogen atoms of the alkyl group is replaced with a heteroaryl group.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The nomenclature used in this application is generally based on the IUPAC recommendations. For example, a compound of Formula (I) wherein $R_1$ is hydrogen; $R_2$ is 2-(4-chlorophenyl)ethyl; $R_3$ is hydrogen; and $R_4$ is 4-methylsulfonylphenyl, is named (±)-trans-N-{2-[2-(4-chlorophenyl)ethylamino]-cyclopentyl}-4-methanesulfonylbenzamide.

Representative compounds of Formula (I) are shown in the following table.

| Compound Number | Structure | M.P. (° C.) |
|---|---|---|
| 1 | 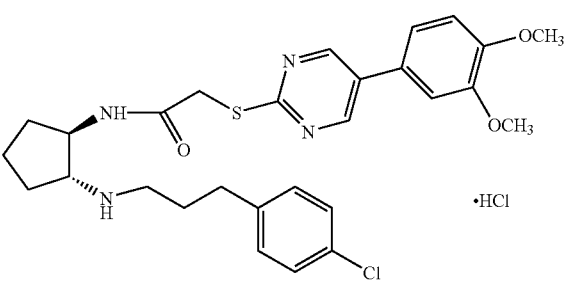 •HCl | 95.3–111.3 |
| 2 | 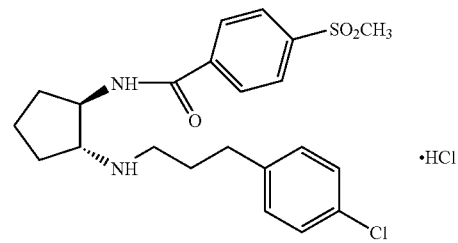 •HCl | 192.3–196.8 |
| 3 | 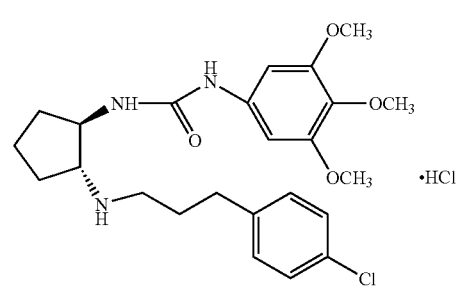 •HCl | 91.3–96.0 |
| 4 | 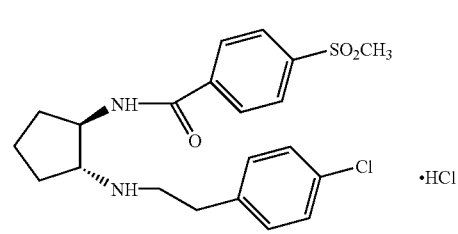 •HCl | 221.8–222.7 |

-continued

| Compound Number | Structure | M.P. (° C.) |
|---|---|---|
| 5 | 3,4,5-trimethoxyphenyl urea of (1R,2S)-N-methyl-N-[3-(4-chlorophenyl)propyl]-cyclopentane-1,2-diamine · HCl | 75.0–82.0 |
| 6 | 3,4,5-trimethoxyphenyl urea of (1R,2S)-N-methyl-N-[2-(4-chlorophenyl)ethyl]-cyclopentane-1,2-diamine · HCl | 97.0–105.0 |
| 7 | 4-(methylsulfonyl)benzamide of (1R,2S)-N-methyl-N-[2-(4-chlorophenyl)ethyl]-cyclopentane-1,2-diamine · HCl | 179.0–179.3 |
| 8 | 4-(methylsulfonyl)benzamide of (1R,2S)-N-methyl-N-[3-(4-chlorophenyl)propyl]-cyclopentane-1,2-diamine · HCl | 109.0–113.0 |
| 9 | 2-{[5-(3,4-dimethoxyphenyl)pyrimidin-2-yl]thio}acetamide of (1R,2S)-N-methyl-N-[3-(4-chlorophenyl)propyl]-cyclopentane-1,2-diamine · HCl | 91.5–98.5 |

-continued

| Compound Number | Structure | M.P. (° C.) |
|---|---|---|
| 10 | (structure) ·HCl | 123.7–125.3 |
| 11 | (structure) ·HCl | 97.0–101.5 |
| 12 | (structure) ·HCl | 181.3–185.6 |

PREFERRED EMBODIMENTS

While the broadest definition of this invention is set forth in the Summary of the Invention, certain compounds of Formula (I) are preferred.

A preferred compound of the invention is a compound of Formula (I) wherein $R_1$ is hydrogen or methyl.

A preferred compound of the invention is a compound of Formula (I) wherein $R_2$ is phenylalkyl, wherein the phenyl is optionally substituted with one, two or three substituents independently selected from the group consisting of alkyl, halo, cyano, nitro, alkoxy, haloalkoxy, hydroxy, amino, acylamino, alkylamino, and dialkylamino.

A preferred compound of the invention is a compound of Formula (I) wherein $R_2$ is phenylalkyl, wherein the phenyl is substituted with one, two or three substituents independently selected from the group consisting of alkyl, halo, cyano, nitro, alkoxy, haloalkoxy, hydroxy, amino, acylamino, alkylamino, and dialkylamino.

A preferred compound of the invention is a compound of Formula (I) wherein $R_2$ is phenylalkyl, wherein the phenyl is substituted with one, two or three halo substituents.

A preferred compound of the invention is a compound of Formula (I) wherein $R_2$ is phenylalkyl, wherein the phenyl is substituted with one or two halo substituents.

A preferred compound of the invention is a compound of Formula (I) wherein $R_2$ is phenylalkyl, wherein the phenyl is substituted with one halo substituent.

A more preferred compound of the invention is a compound of Formula (I) wherein $R_2$ is (4-chlorophenyl)alkyl.

An even more preferred compound of the invention is a compound of Formula (I) wherein $R_2$ is 2-(4-chlorophenyl)ethyl, or 3-(4-chlorophenyl)propyl.

A preferred compound of the invention is a compound of Formula (I) wherein $R_3$ is hydrogen or methyl, preferably hydrogen.

A preferred compound of the invention is a compound of Formula (I) wherein $R_3$ is, alkyl, acyl, aryl, or arylalkyl.

A preferred compound of the invention is a compound of Formula (I) wherein W is absent.

A preferred compound of the invention is a compound of Formula (I) wherein W is alkylene.

A preferred compound of the invention is a compound of Formula (I) wherein X is absent.

A preferred compound of the invention is a compound of Formula (I) wherein X is carbonyl (—C(=O)—), oxy (—O—), —S(O)$_n$—, or —N($R_a$)—.

A preferred compound of the invention is a compound of Formula (I) wherein X is thio.

A preferred compound of the invention is a compound of Formula (I) wherein Y is aryl.

A preferred compound of the invention is a compound of Formula (I) wherein Y is heteroaryl.

A preferred compound of the invention is a compound of Formula (I) wherein —Y-Z is 4-methylsulfonylphenyl; or 3,4,5-trimethoxyphenyl.

A preferred compound of the invention is a compound of Formula (I) wherein $R_4$ is 4-methylsulfonylphenyl; 3,4,5-trimethoxyphenylamino; or 5-(3,4-dimethoxyphenyl)pyrimidin-2-ylthiomethyl.

A preferred compound of the invention is a compound of Formula (I) wherein Z is hydrogen.

A preferred compound of the invention is a compound of Formula (I) wherein Z is aryl, heteroaryl, aryloxy, heteroaryloxy, or arylalkyl, or heteroarylalkylene.

A preferred compound of the invention is a compound of Formula (I) wherein

A particularly preferred compound of the invention is:

(±)-trans-N-{2-[3-(4-Chlorophenyl)propylamino]cyclopentyl}-2-[5-(3,4-dimethoxyphenyl)pyrimidin-2-ylsulfanyl]acetamide;

(±)-trans-N-{2-[3-(4-Chlorophenyl)propylamino]cyclopentyl}-4-methanesulfonylbenzamide;

(±)-trans-1-{2-[3-(4-Chlorophenyl)propylamino]-cyclopentyl}-3-(3,4,5-trimethoxyphenyl)urea;

(±)-trans-N-{2-[2-(4-Chlorophenyl)ethylamino]cyclopentyl}-4-methanesulfonylbenzamide;

(±)-trans-1-(2-{[3-(4-Chlorophenyl)propyl]methylamino}-cyclopentyl)-3-(3,4,5-trimethoxyphenyl)urea;

(±)-trans-1-(2-{[2-(4-Chlorophenyl)ethyl]methylamino}cyclopentyl)-3-(3,4,5-trimethoxyphenyl)urea;

(±)-trans-N-(2-{[2-(4-Chlorophenyl)ethyl]methylamino}-cyclopentyl)-4-methanesulfonylbenzamide;

(±)-trans-N-(2-{[3-(4-Chlorophenyl)propyl]methylamino}-cyclopentyl)-4-methanesulfonylbenzamide;

(±)-trans-N-(2-{[3-(4-Chlorophenyl)propyl]methylamino}-cyclopentyl)-2-[5-(3,4-dimethoxyphenyl)pyrimidin-2-ylsulfanyl]acetamide;

(±)-trans-N-(2-{[2-(4-Chlorophenyl)ethyl]methylamino}-cyclopentyl)-2-[5-(3,4-dimethoxyphenyl)pyrimidin-2-ylsulfanyl]acetamide;

(±)-trans-1-{2-[2-(4-Chlorophenyl)ethylamino]cyclopentyl}-3-(3,4,5-trimethoxyphenyl)urea; or (±)-trans-N-{2-[2-(4-Chlorophenyl)ethylamino]cyclopentyl}-2-[5-(3,4-dimethoxyphenyl) pyrimidin-2-ylsulfanyl]acetamide;

or a pharmaceutically acceptable salt thereof.

General Synthetic Scheme

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Enika-Chemie, or Sigma (St. Louis, Mo., USA), Maybridge (Dist: Ryan Scientific, P.O. Box 6496, Columbia, S.C. 92960), Bionet Research Ltd., (Cornwall PL32 9QZ, UK), Menai Organics Ltd., (Gwynedd, N. Wales, UK), Butt Park Ltd., (Dist. Interchim, Montlucon Cedex, France) or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 1992), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Synthesis of Compounds of Formula (I)

In general, compounds of Formula (I) wherein $R_1$ is H and $R_2$ is 2-(4-chlorophenyl)ethyl or 3-(4-chlorophenyl)propyl can be prepared as illustrated in the following scheme.

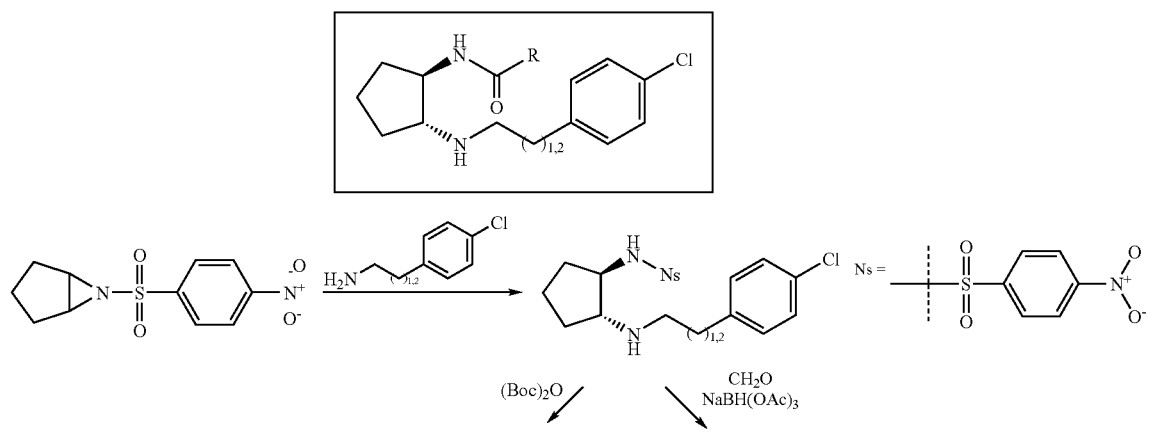

-continued
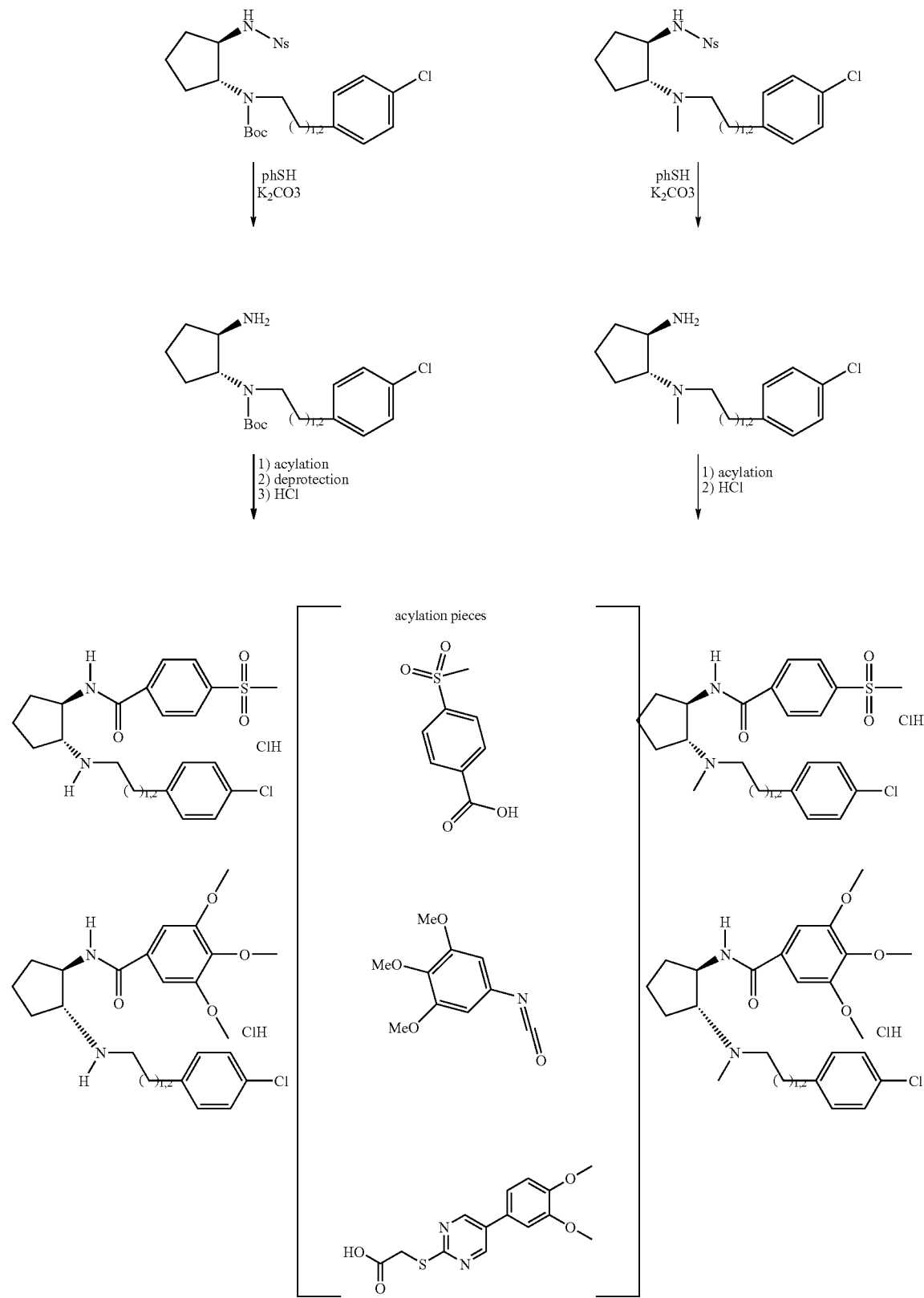

-continued

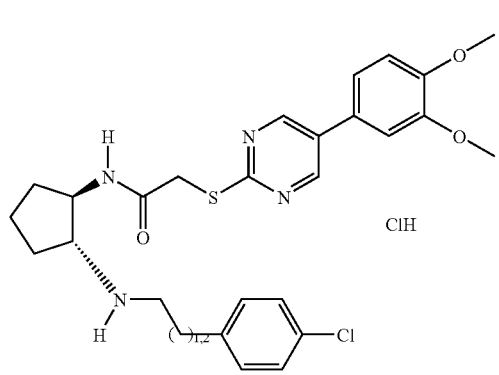

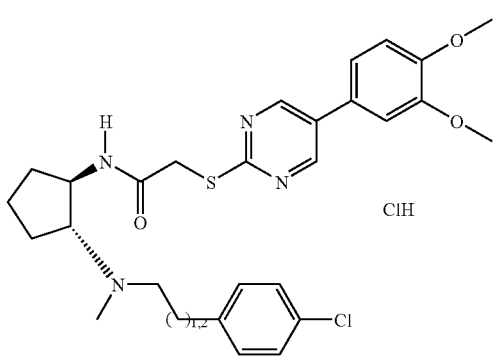

Thus, the invention also provides a method for preparing a compound of Formula (I), wherein $R_1$ is hydrogen, comprising de-protecting a corresponding compound of Formula (III):

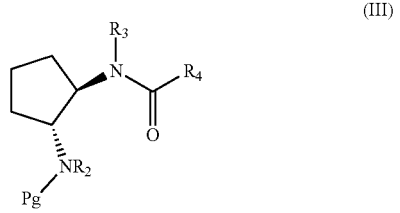

(III)

wherein Pg is a nitrogen protecting group.

The invention also provides a method for preparing a compound of Formula (I), wherein $R_1$ is alkyl, comprising acylating a corresponding compound of Formula (V):

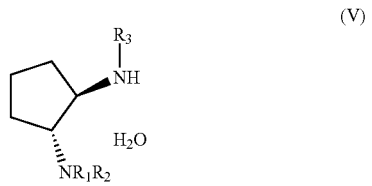

(V)

with the requisite carboxylic acid derivative, R—C(=O)-L where L is a leaving group. Carboxylic acid derivatives that can be used in the method of the invention include carboxylic acids, as well as activated carboxylic acid derivatives (e.g. carboxylic acid chlorides, bromides, or anhydrides). Suitable conditions and reagents for acylating amines are well known in the art. For example, see "Advanced Organic Chemistry, Reactions, Mechanisms, And Structure" Jerry March, fourth ed., (1992), John Wiley & Sons, New York.

The invention also provides a method for preparing a compound of Formula (III):

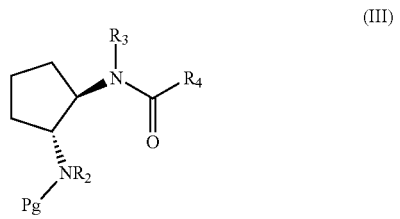

(III)

wherein: Pg is a nitrogen protecting group; $R_2$ is arylalkyl; $R_3$ is hydrogen, alkyl, acyl, aryl, or arylalkyl; $R_4$ is —W—X—Y-Z; W is absent or alkylene; X is absent, carbonyl, oxy, —S(O)$_n$—, or —N($R_a$)—; Y is arylene or heteroarylene; Z is hydrogen, aryl, heteroaryl, aryloxy, heteroaryloxy, arylalkyl, or heteroarylalkylene; $R_a$ is hydrogen, alkyl, acyl, aryl, arylalkyl, alkoxycarbonyl, or benzyloxycarbonyl; comprising acylating a corresponding compound of Formula (IV):

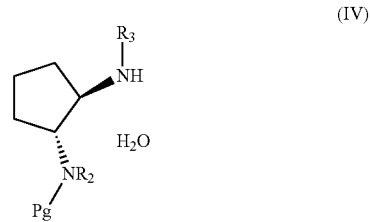

(IV)

with the requisite carboxylic acid derivative, R—C(=O)-L where L is a leaving group.

An intermediate that is particularly useful for preparing a compound of Formula (I) is a compound of Formula (II):

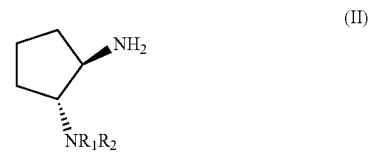

(II)

wherein $R_1$ and $R_2$ have any of the values or preferred values provided herein.

Another intermediate that is particularly useful for preparing a compound of Formula (I) is a compound of Formula (III):

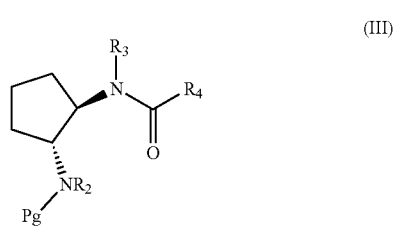

(III)

wherein $R_2$–$R_4$ have any of the values or preferred values provided herein; and Pg is a nitrogen protecting group (e.g. tert-butoxycarbonyl).

Another intermediate that is particularly useful for preparing a compound of Formula (I) is a compound of Formula (IV):

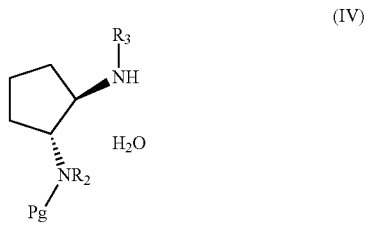

wherein $R_2$ and $R_3$ have any of the values or preferred values provided herein; and Pg is a nitrogen protecting group (e.g. tert-butoxycarbonyl).

Another intermediate that is particularly useful for preparing a compound of Formula (I) is a compound of Formula (V):

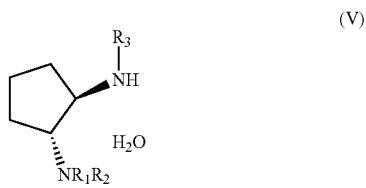

wherein $R_2$ and $R_3$ have any of the values or preferred values provided herein; and $R_1$ is alkyl.

Experimental Section

General. Unless otherwise noted, all non-aqueous reactions were run under a nitrogen atmosphere and $Na_2SO_4$ was used to dry all organic layers. Purifications were typically carried out by flash chromatography on silica gel (230–400 mesh) or preparative TLC on Uniplate Silica Gel GF PLC Plates (20×20 cm, 1000 microns) from Analtech, Inc., Newark, Del. Alumina used was basic with 6 wt % $H_2O$ (Brockmann III). Melting points taken in capillary tubes are uncorrected. IR spectra were determined in KBr. NMR spectra were run in $CDCl_3$, unless otherwise indicated. $^1H$ NMR spectra were recorded on 300 MHz instruments and $^{13}C$ NMR spectra were recorded at 75.5 MHz. Mass spectral analyses were accomplished using electrospray ionization. Analytical reverse-phase HPLC was performed on Shimadzu system equipped with a diode array spectrometer (range 190–300 nm; Hewlett Packard). The stationary phase was a Zorbax SB-Phenyl Rapid Resolution column (4.6 mm×50 mm; Hewlett Packard), mobile phase A was 0.1% trifluoroacetic acid, and mobile phase B was $CH_3CN$. A flow rate of 2.5 mL/min with a linear gradient of 20–55% B in 5 min and then 55–20% B in 5 min was employed.

General Utility

The compounds of the invention are CCR-3 receptor antagonists and inhibit eosinophil recruitment by CCR-3 chemokines such as RANTES, eotaxin, MCP-2, MCP-3 and MCP-4. Compounds of this invention and compositions containing them are useful in the treatment of eosiniphil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia); inflammatory bowel diseases (e.g., Crohn's disease and ulcerative colitis); and psoriasis and inflammatory dermatoses such as dermatitis and eczema.

Testing

The CCR-3 antagonistic activity of the compounds of this invention can be measured by in vitro assays such as ligand binding and chemotaxis assays as described in more detail in Examples 14, 15 and 16. In vivo activity may be assayed in the Ovalbumin induced Asthma in Balb/c Mice Model as described in more detail in Example 17.

Administration and Pharmaceutical Composition

In general, the compounds of this invention can be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.01–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, inhalation (e.g., intranasal or oral inhalation) or parenteral (e.g., intramuscular, intravenous or subcutaneous) administration. A preferred manner of administration is oral using a convenient daily dosage regimen which can be adjusted according to the degree of affliction. Compositions can take the form of tablets, pills, capsules, semisolids, powders, sustained release Formulations, solutions, suspensions, liposomes, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be Formulated as liquid solutions or suspensions, aerosol propellants or dry powder and loaded into a suitable dispenser for administration. There are three types of pharmaceutical inhalation devices—nebulizer inhalers, metered-dose inhalers (MDI) and dry powder inhalers (DPI). Nebulizer devices produce a stream of high velocity air that causes the therapeutic agents (which has been Formulated in a liquid form) to spray as a mist which is carried into the patient's respiratory tract. MDI's typically have the Formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

For liposomal formulations of the drug for parenteral or oral delivery the drug and the lipids are dissolved in a suitable organic solvent e.g. tert-butanol, cyclohexane (1% ethanol). The solution is lyophilized and the lipid mixture is suspended in an aqueous buffer an allowed to form a liposome. If necessary, the liposome size can be reduced by sonification. (see, Frank Szoka, Jr. and Demetrios Papahadjopoulos, "Comparative Properties and Methods of Preparation of Lipid Vesicles (Liposomes)", Ann. Rev. Biophys. Bioeng., 9:467–508 (1980), and D. D. Lasic, "Novel Applications of Liposomes", Trends in Biotech., 16:467–608, (1998)).

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the Formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 13.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

General Procedure A (Urea Formation Using Isocyanates)

A 0.1–0.6 M solution of the amine (1 equiv) in $CH_2Cl_2$ or $CH_2Cl_2$ and DMF at 0–20° C. is treated with the specified isocyanate (1.1–2 equiv), stirred for 0.5–1.5 h, and partitioned between $CH_2Cl_2$ and saturated $NaHCO_3$. The aqueous phase is extracted with $CH_2Cl_2$ and the extracts are dried and concentrated. The crude urea is purified by column chromatography or preparative TLC or used in the next step without further purification.

General Procedure B (Urea Formation Using Isocyanates Followed by Hydrochloride Salt Formation)

A 0.1–0.6 M solution of the amine (1 equiv) in $CH_2Cl_2$ or $CH_2Cl_2$ and DMF at 0–20° C. is treated with the specified isocyanate (1.1–2 equiv), stirred for 0.5–1.5 h, and partitioned between $CH_2Cl_2$ and saturated $NaHCO_3$. The aqueous phase is extracted with $CH_2Cl_2$ and the extracts are dried and concentrated. The crude urea is purified by column chromatography or preparative TLC or used in the next step without further purification. A solution of the free base in $CH_2Cl_2$ is treated with 1 N HCl in $Et_2O$ and concentrated to give the hydrochloride salt.

General Procedure C (Amide Formation Using 1-Hydroxybenzotriazole and 1-(3-Dimethylamino-propyl)-3-ethylcarbodiimide Hydrochloride)

A 0.1–0.4 M solution of the amine (1 equiv) and the specified carboxylic acid (1.2–1.5 equiv) in $CH_2Cl_2$ at 0° C. is treated successively with 1-hydroxybenzotriazole hydrate (HOBt) (0.2–0.5 equiv) and 1-[3-(dimethylamino)propyl]-3-ethylcarbodiimide hydrochloride (DEC) (1.3–2 equiv), stirred at 0–20° C. for 2–72 h, and partitioned between $CH_2Cl_2$ and saturated $NaHCO_3$. The aqueous phase is extracted with $CH_2Cl_2$ and the extracts are dried and concentrated. The crude amide is purified by column chromatography and/or preparative TLC.

General Procedure D (Amide Formation Using 1-Hydroxybenzotriazole and 1-(3-Dimethylamino-propyl)-3-ethylcarbodiimide Hydrochloride Followed by Hydrochloride Salt Formation)

A 0.1–0.4 M solution of the amine (1 equiv) and the specified carboxylic acid (1.2–1.5 equiv) in $CH_2Cl_2$ at 0° C. is treated successively with 1-hydroxybenzotriazole hydrate (HOBt) (0.2–0.5 equiv) and 1-[3-(dimethylamino)propyl]-3-ethylcarbodiimide hydrochloride (DEC) (1.3–2 equiv), stirred at 0–20° C. for 2–72 h, and partitioned between $CH_2Cl_2$ and saturated $NaHCO_3$. The aqueous phase is extracted with $CH_2Cl_2$ and the extracts are dried and concentrated. The crude amide is purified by column chromatography and/or preparative TLC. A solution of the free base in $CH_2Cl_2$ is treated with 1 N HCl in $Et_2O$ and concentrated to give the hydrochloride salt.

Example 1

(±)-trans-N-{2-[3-(4-Chlorophenyl)propylamino]
cyclopentyl}-2-[5-(3,4-dimethoxyphenyl)pyrimidin-
2-ylsulfanyl]acetamide hydrochloride

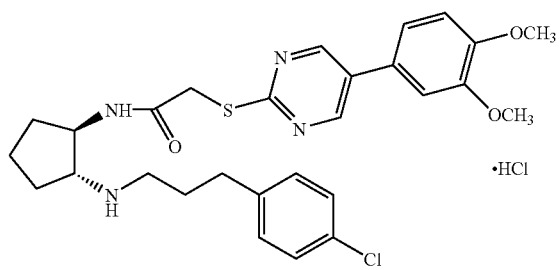

A solution of (±)-trans-[3-(4-chlorophenyl)propyl]-(2-{2-[5-(3,4-dimethoxy-phenyl)pyrimidin-2-ylsulfanyl]acetylamino}cyclopentyl)carbamic acid tert-butyl ester (185 mg, 80% pure, ~0.23 mmol) in 10% HCl/MeOH (30 mL) was stirred at room temperature overnight. The MeOH was evaporated and the residue was partitioned between CH$_2$Cl$_2$ and saturated NaHCO$_3$. The aqueous phase was extracted with CH$_2$Cl$_2$ and the extracts were washed with brine, dried and concentrated. Purification of the residue by preparative TLC with 10:0.95:0.05 CH$_2$Cl$_2$:MeOH:NH$_4$OH gave the free base (98 mg, 0.18 mmol) as a colorless oil. A solution of the free base in CH$_2$Cl$_2$ was treated with 1 N HCl in Et$_2$O (0.3 mL, 0.3 mmol) and concentrated to give the product (104 mg, 67% from (±)-trans-(2-amino-cyclopentyl)-[3-(4-chloro-phenyl)-propyl]-carbamic acid tert-butyl ester) as a yellow solid: mp 95.3–111.3° C.; MS m/z 541 (M+1)$^+$.

The intermediate (±)-trans-[3-(4-chlorophenyl)propyl]-(2-{2-[5-(3,4-dimethoxyphenyl)pyrimidin-2-ylsulfanyl]acetylamino}cyclopentyl)carbamic acid tert-butyl ester was prepared as follows.

Step A: Preparation of 6-(4-nitrobenzenesulfonyl)-6-aza-bicyclo[3.1.0]hexane

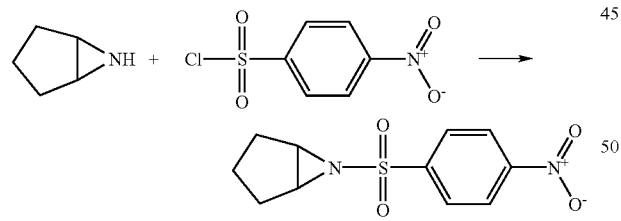

A solution of 4-nitro-benzenesulfonyl chloride (10.2 g, 46.0 mmol) in CH$_2$Cl$_2$ (15 mL) at −20° C. was treated dropwise during 20 min with a solution of 6-aza-bicyclo [3.1.0]hexane (3.8 g, 45.8 mmol) [Zhang, Z. da; Scheffold, R. *Helv. Chim. Acta* 1993, 76, 2602] and Et$_3$N (7.0 mL, 50.4 mmol) in CH$_2$Cl$_2$ (35 mL), allowed to warm to 10° C. over 30 min, and partitioned between CH$_2$Cl$_2$ and 1 N NaH$_2$PO$_4$. The aqueous phase was extracted with CH$_2$Cl$_2$ and the extracts were washed with H$_2$O, 5% aqueous NaHCO$_3$ and brine, dried (MgSO$_4$) and concentrated. The residue was crystallized in 12:4:3 hexane:CH$_2$Cl$_2$:methyl tert-butyl ester to give the product (10.1 g, 82%) as a light brown solid: MS m/z 269.1 (M+1)$^+$.

Step B: Preparation of (±)-trans-N-{2-[3-(4-chlorophenyl) propylamino]-cyclopentyl}-4-nitro-benzenesulfonamide

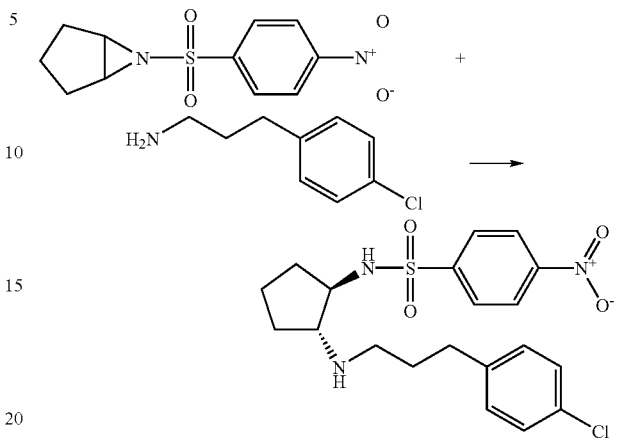

A solution of 6-(4-nitrobenzenesulfonyl)-6-aza-bicyclo [3.1.0]hexane (2.7 g, 10 mmol), 3-(4-chlorophenyl)propylamine (1.7 g, 10 mmol) [Fujimura, K.-i.; Matsumoto, J; Niwa, M.; Kobayashi, T.; Kawashima, Y.; In, Y.; Ishida, T. *Bioorg. Med. Chem.* 1997, 5, 1675] and Et$_3$N (0.27 mL, 2 mmol) in THF (10 mL) was refluxed for 15 hours, allowed to cool to room temperature, and concentrated. Chromatography of the residue with 100:0.95:0.05–50:0.95:0.05 CH$_2$Cl$_2$:MeOH:NH$_4$OH gave the product (1.88 g, 43%) as a brown foam: MS m/z 438.1 (M+1)$^+$.

Step C: Preparation of (±)-trans-[3-(4-chlorophenyl)propyl]-[2-(4-nitro-benzenesulfonylamino)-cyclopentyl]-carbamic acid tert-butyl ester

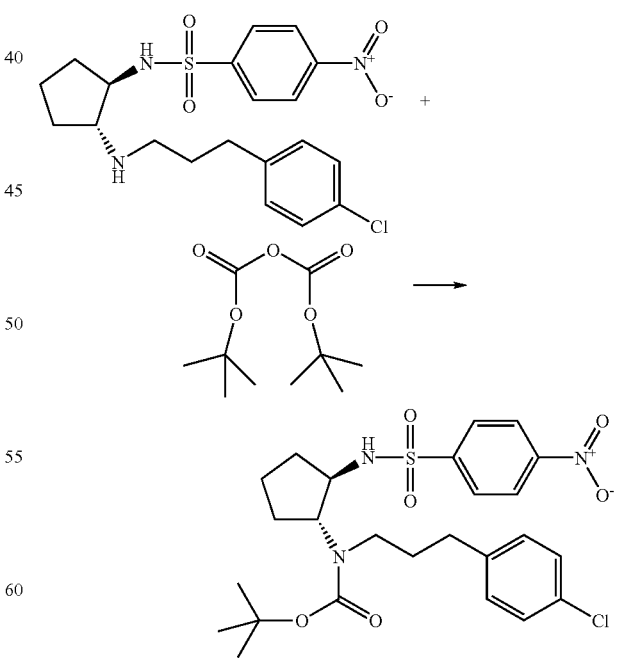

A solution of (±)-trans-N-{2-[3-(4-chlorophenyl)propylamino]-cyclopentyl}-4-nitro-benzenesulfonamide (920 mg, 2.1 mmol) and Et$_3$N (0.35 mL, 2.5 mmol) in CH$_2$Cl$_2$ (15 mL) was treated with di-tert-butyl dicarbonate (458 mg, 2.1 mmol) and stirred at room temperature for 23 h, during which additional Et₃N (0.2 mL, 1.43 mmol) and di-tert-butyl dicarbonate (200 mg, 0.92 mmol) was added. The reaction mixture was partitioned between CH₂Cl₂ and saturated NaHCO₃, the aqueous phase was extracted with CH₂Cl₂, and the extracts were washed with brine, dried (MgSO₄) and concentrated to give 1.34 g of the product as a brown oil which was used directly in the next step: MS m/z 538.1 $(M+1)^+$.

Step D: Preparation of (±)-trans-(2-aminocyclopentyl)-[3-(4-chlorophenyl)propyl]-carbamic acid tert-butyl ester

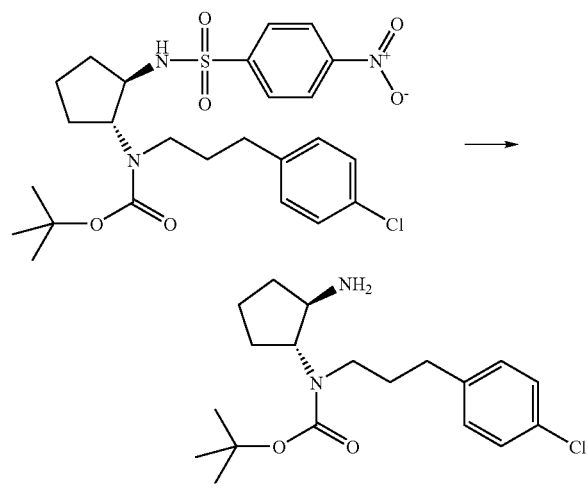

A mixture of (±)-trans-[3-(4-chlorophenyl)propyl]-[2-(4-nitro-benzenesulfonylamino)cyclopentyl]carbamic acid tert-butyl ester (1.34 g, approximately 2.1 mmol), PhSH (0.86 mL, 8.4 mmol), K₂CO₃ (1.5 g, 10.9 mmol) and 40:1 CH₃CN:DMSO (40 mL) was stirred at 80° C. overnight and allowed to cool to room temperature. The white solid was filtered off and the filtrate was concentrated. The residue was partitioned between CH₂Cl₂ and H₂O and the organic phase was washed with H₂O and brine, dried and concentrated. Chromatography of the residue with CH₂Cl₂ followed by 100:0.95:0.05–5:0.95:0.05 CH₂Cl₂:MeOH:NH₄OH gave the product (571 mg, 77%) as a yellow oil: MS m/z 353.2 $(M+1)^+$.

Step E: Preparation of (±)-trans-[3-(4-chlorophenyl)propyl]-(2-{2-[5-(3,4-dimethoxyphenyl)pyrimidin-2-ylsulfanyl]acetylamino}cyclopentyl)carbamic acid tert-butyl ester

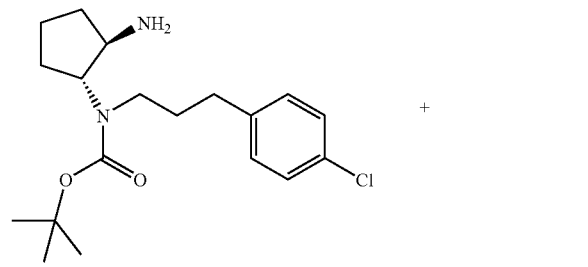

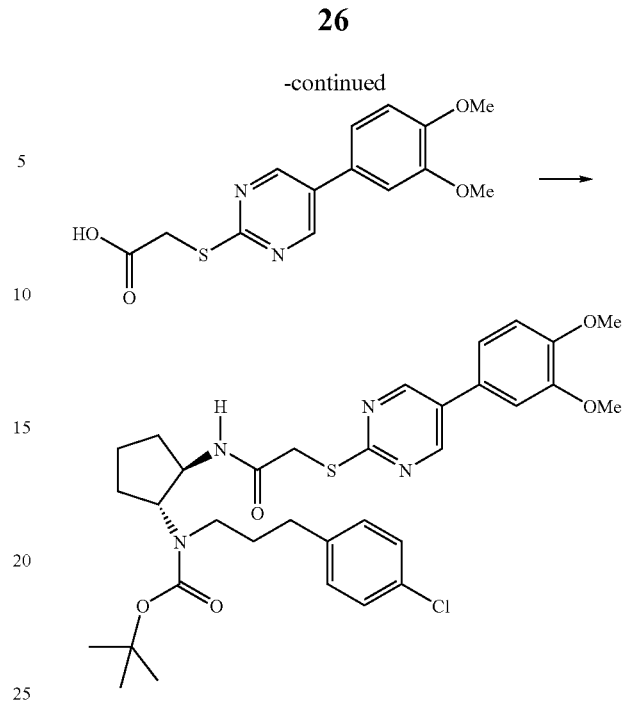

Using General Procedure C, (±)-trans-(2-aminocyclopentyl)-[3-(4-chloro-phenyl)propyl]carbamic acid tert-butyl ester (95 mg, 0.27 mmol) and [5-(3,4-dimethoxyphenyl)pyrimidin-2-ylsulfanyl]acetic acid (90 mg, 0.30 mmol) (prepared as described in Rogers, D. H., Saunders, J., and Williams, J. P. "Preparation of N-Pyrrolidinylmethylalkanoamides and analogs as CCR-3 receptor antagonists; DE19955794 A1 20000531) were coupled in CH₂Cl₂ (3 mL) using HOBt (8 mg, 0.06 mmol) and DEC (77 mg, 0.40 mmol) at 0° C. for 2 h. Purification of the crude product by preparative TLC with 100:0.95:0.05 CH₂Cl₂:MeOH:NH₄OH gave 185 mg of the product (~80% pure) as a colorless oil: MS m/z 641 $(M+1)^+$.

Example 2

(±)-trans-N-{2-[3-(4-Chlorophenyl)propylamino]cyclopentyl}-4-methanesulfonylbenzamide hydrochloride

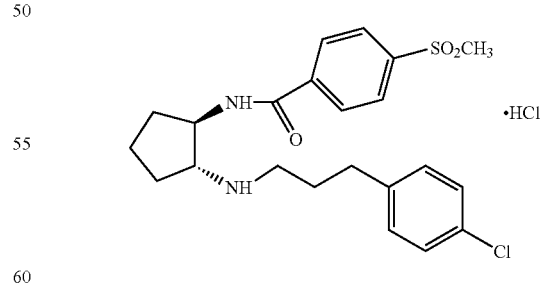

A solution of (±)-trans-[3-(4-chlorophenyl)propyl]-[2-(4-methanesulfonyl-benzoylamino)cyclopentyl] carbamic acid tert-butyl ester in 10% HCl/MeOH (25 mL) was stirred at room temperature overnight. The MeOH was evaporated and the residue was partitioned between CH₂Cl₂ and saturated NaHCO₃. The aqueous phase was extracted with CH$_2$Cl$_2$ and the extracts were washed with brine, dried and concentrated. Purification of the residue by preparative TLC with 10:0.95:0.05 CH$_2$Cl$_2$:MeOH:NH$_4$OH gave the free base (116 mg, 0.27 mmol) as a colorless oil. A solution of the free base in CH$_2$Cl$_2$ was treated with 1 N HCl in Et$_2$O (0.3 mL, 0.3 mmol) and concentrated to give the product (123 mg, 61%) as a white solid: mp 192.3–196.8° C.; MS m/z 435 (M+1)$^+$.

The intermediate (±)-trans-[3-(4-chlorophenyl)propyl]-[2-(4-methanesulfonylbenzoylamino)cyclopentyl]carbamic acid tert-butyl ester was prepared as follows.

Step A: Preparation of (±)-trans-[3-(4-chlorophenyl)propyl]-[2-(4-methanesulfonylbenzoylamino)cyclopentyl]carbamic acid tert-butyl ester Using General Procedure C, (±)-trans-(2-aminocyclopentyl)-[3-(4-chloro-phenyl)propyl]carbamic acid tert-butyl ester (155 mg, 0.44 mmol) and 4-methanesulfonylbenzoic acid (105 mg, 0.53 mmol) were coupled in CH$_2$Cl$_2$ (3 mL) using HOBt (12 mg, 0.09 mmol) and DEC (106 mg, 0.66 mmol) at 0° C. for 2.5 hours to give 250 mg of (±)-trans-[3-(4-chlorophenyl)propyl]-[2-(4-methanesulfonylbenzoylamino)cyclopentyl]carbamic acid tert-butyl ester as a colorless oil.

Example 3

(±)-trans-1-{2-[3-(4-Chlorophenyl)propylamino]cyclopentyl}-3-(3,4,5-trimethoxyphenyl)urea hydrochloride

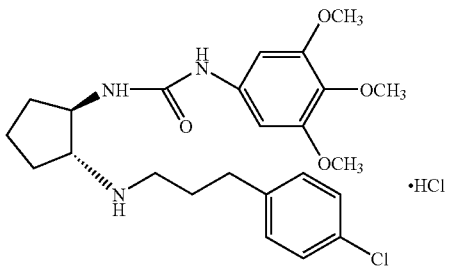

A solution of (±)-trans-[3-(4-chlorophenyl)propyl]-{2-[3-(3,4,5-trimethoxyphenyl)ureido]cyclopentyl}carbamic acid tert-butyl ester (165 mg, 0.29 mmol) in 10% HCl/MeOH (25 mL) was stirred at room temperature overnight. The MeOH was evaporated and the residue was partitioned between CH$_2$Cl$_2$ and saturated NaHCO$_3$. The aqueous phase was extracted with CH$_2$Cl$_2$ and the extracts were washed with brine, dried and concentrated. Purification of the residue by preparative TLC with 10:0.95:0.05 CH$_2$Cl$_2$:MeOH:NH$_4$OH gave the free base as a colorless oil. A solution of the free base in CH$_2$Cl$_2$ was treated with 1 N HCl in Et$_2$O (0.4 mL, 0.4 mmol) and concentrated to give the product (104 mg, 72%) as a tan solid: mp 91.3–96.0° C.; MS m/z 462 (M+1)$^+$.

The intermediate (±)-trans-[3-(4-chlorophenyl)propyl]-{2-[3-(3,4,5-trimethoxyphenyl)ureido]cyclopentyl}carbamic acid tert-butyl ester was prepared as follows.

Step A: Preparation of (±)-trans-[3-(4-chlorophenyl)propyl]-{2-[3-(3,4,5-trimethoxyphenyl)ureido]cyclopentyl}carbamic acid tert-butyl ester

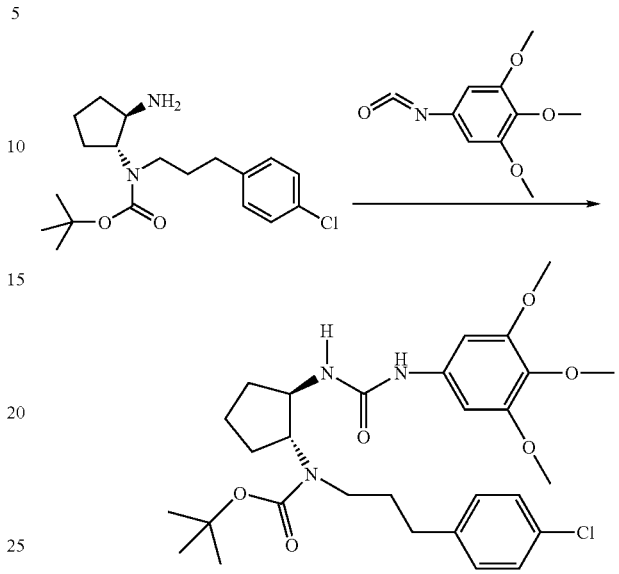

Using General Procedure A, (±)-trans-(2-aminocyclopentyl)-[3-(4-chlorophenyl)propyl]-carbamic acid tert-butyl ester (152 mg, 0.43 mmol) and 5-isocyanato-1,2,3-trimethoxybenzene (108 mg, 0.52 mmol) were coupled in CH$_2$Cl$_2$ (2 mL) at 0° C. for 1.5 h. Purification of the crude product by preparative TLC with 10:0.95:0.05 CH$_2$Cl$_2$:MeOH:NH$_4$OH gave the product (168 mg, 70%) as a colorless oil: MS m/z 562.2 (M+1)$^+$.

Example 4

(±)-trans-N-{2-[2-(4-Chlorophenyl)ethylamino]cyclopentyl}-4-methanesulfonylbenzamide hydrochloride

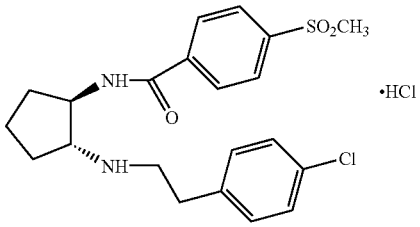

Using procedures similar to those described in Example 3, except replacing the (±)-trans-[3-(4-chlorophenyl)propyl]-{2-[3-(3,4,5-trimethoxyphenyl)ureido]-cyclopentyl}carbamic acid tert-butyl ester used therein with (±)-trans-[2-(4-chlorophenyl)ethyl]-[2-(4-methanesulfonylbenzoylamino)cyclopentyl]carbamic acid tert-butyl ester, the title compound was prepared; MS m/z 421 (M+1)$^+$.

The intermediate (±)-trans-[2-(4-chlorophenyl)ethyl]-[2-(4-methanesulfonylbenzoylamino)cyclopentyl]carbamic acid tert-butyl ester was prepared using procedures similar to those described in Example 1, except replacing the 3-(4-chlorophenyl)propylamine used in Step B with 2-(4-chlorophenyl)-ethylamine, and replacing the acid used in Step E with the requisite acid.

Example 5

(±)-trans-1-(2-{[3-(4-Chlorophenyl)propyl]methylamino}-cyclopentyl)-3-(3,4,5-trimethoxyphenyl)urea hydrochloride

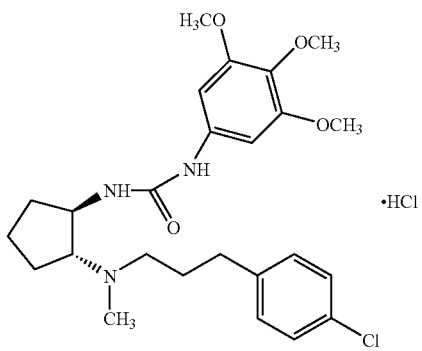

Using General Procedure B above, the title compound was prepared from (±)-trans-N-[3-(4-chlorophenyl)propyl]-N-methylcyclopentane-1,2-diamine and 5-isocyanato-1,2,3-trimethoxybenzene; MS m/z 476 (M+1)+.

The intermediate (±)-trans-N-[3-(4-chlorophenyl)propyl]-N-methylcyclopentane-1,2-diamine was prepared as follows.

Step A: Preparation of (±)-trans-N-(2-{[3-(4-chlorophenyl)propyl]methylamino}-cyclopentyl)-4-nitrobenzenesulfonamide

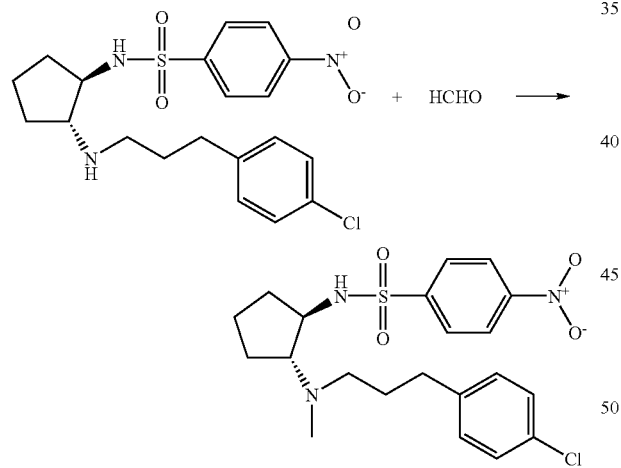

A solution of (±)-trans-N-{2-[3-(4-chlorophenyl)propylamino]cyclopentyl}-4-nitrobenzenesulfonamide (940 mg, 2.15 mmol) and 37% aqueous HCHO (0.16 mL, 2.15 mmol) in 1,2-dichloroethane (10 mL) was treated with NaBH(OAc)$_3$ (456 mg, 8.6 mmol) and stirred at room temperature for 24 hours, during which additional 37% aqueous HCHO (0.05 mL, 0.67 mmol) was added. The reaction mixture was partitioned between 1,2-dichloroethane and saturated NaHCO$_3$, the aqueous phase was extracted with EtOAc, and the extracts were washed with brine, dried and concentrated. Chromatography of the residue with 25:0.95:0.05 CH$_2$Cl$_2$:MeOH:NH$_4$OH gave the product (965 mg, 100%) as a yellow oil: MS m/z 452.1 (M+1)+.

Step B: Preparation of (±)-trans-N-[3-(4-chlorophenyl)propyl]-N-methyl-cyclopentane-1,2-diamine

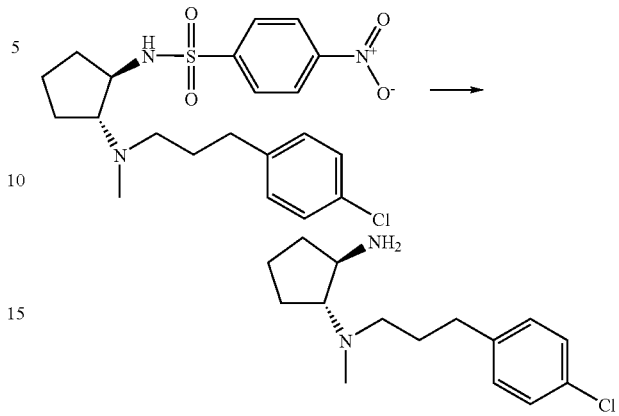

A mixture of (±)-trans-N-(2-{[3-(4-chlorophenyl)propyl]methylamino}-cyclopentyl)-4-nitrobenzenesulfonamide (960 mg, 2.12 mmol), PhSH (1.09 mL, 10.6 mmol), K$_2$CO$_3$ (1.9 g, 13.8 mmol) and 40:1 CH$_3$CN:DMSO (40 mL) was stirred at 80° C. overnight and allowed to cool to room temperature. The white solid was filtered off and the filtrate was concentrated. The residue was partitioned between CH$_2$Cl$_2$ and H$_2$O, the organic phase was washed with H$_2$O and brine, dried and concentrated. Chromatography of the residue with 100% CH$_2$Cl$_2$ followed by 40:0.95:0.05–5:0.95:0.05 CH$_2$Cl$_2$:MeOH:NH$_4$OH gave the product (300 mg, 53%) as a brown oil: MS m/z 267.1 (M+1)+.

Example 6

(±)-trans-1-(2-{[2-(4-Chlorophenyl)ethyl]methylamino}cyclopentyl)-3-(3,4,5-trimethoxyphenyl)urea hydrochloride

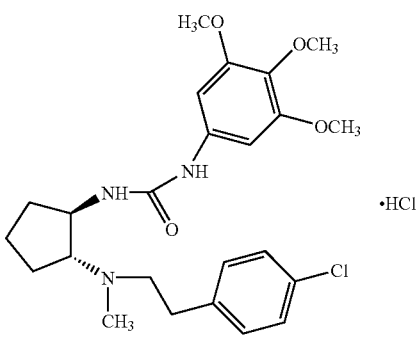

Using General Procedure B above, the title compound was prepared from (±)-trans-N-[2-(4-chlorophenyl)ethyl]-N-methylcyclopentane-1,2-diamine and 5-isocyanato-1,2,3-trimethoxybenzene MS m/z 462 (M+1)+.

The intermediate (±)-trans-N-[2-(4-chlorophenyl)ethyl]-N-methylcyclopentane-1,2-diamine was prepared as described in Example 5, except replacing the (±)-trans-N-{2-[3-(4-chlorophenyl)propylamino]cyclopentyl}-4-nitrobenzenesulfonamide used in Step A with (±)-trans-N-{2-[2-(4-chlorophenyl)ethylamino]cyclopentyl}-4-nitrobenzenesulfonamide, which was made by a procedure similar to Example 1, Step B.

Example 7

(±)-trans-N-(2-{[2-(4-Chlorophenyl)ethyl]methylamino}-cyclopentyl)-4-methanesulfonylbenzamide hydrochloride

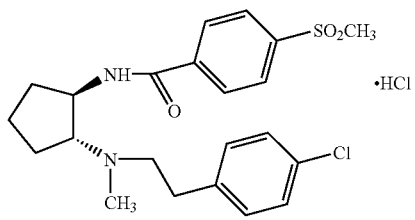

Using General Procedure D, as described in Example 2, Step A, the title compound was prepared from (±)-trans-N-[2-(4-chlorophenyl)ethyl]-N-methylcyclopentane-1,2-diamine and 4-methylsulfonylbenzoic acid MS m/z 435 (M+1)$^+$.

Examples 8–9

Using General Procedure D, the following compounds were prepared from (±)-trans-N-[3-(4-chlorophenyl)propyl]-N-methylcyclopentane-1,2-diamine and the requisite carboxylic acid.

Example 8

(±)-trans-N-(2-{[3-(4-Chlorophenyl)propyl]methylamino}-cyclopentyl)-4-methanesulfonylbenzamide hydrochloride; MS m/z 449 (M+1)$^+$.

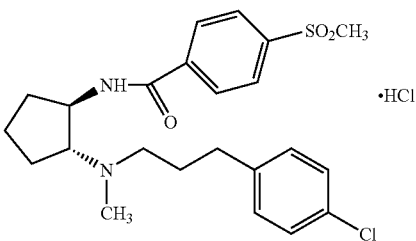

Example 9

(±)-trans-N-(2-{[3-(4-Chlorophenyl)propyl]methylamino}-cyclopentyl)-2-[5-(3,4-dimethoxyphenyl)pyrimidin-2-ylsulfanyl]acetamide hydrochloride; MS ml/z 555 (M+1)$^+$.

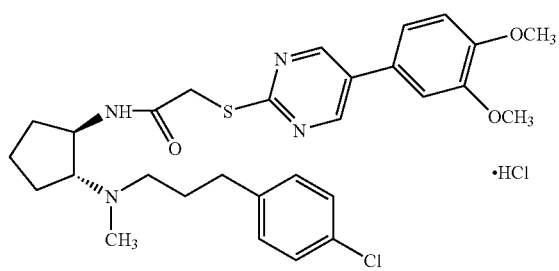

Example 10

(±)-trans-N-(2-{[2-(4-Chlorophenyl)ethyl]methylamino}-cyclopentyl)-2-[5-(3,4-dimethoxyphenyl)pyrimidin-2-ylsulfanyl]acetamide hydrochloride; MS m/z 541 (M+1)$^+$.

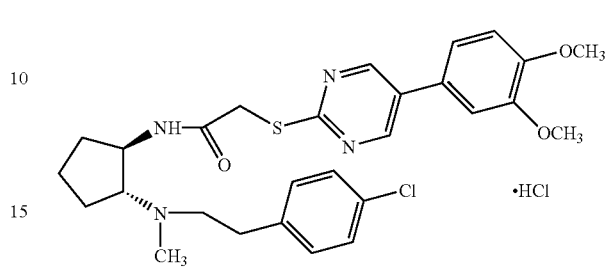

The title compound was prepared from (±)-trans-N-[2-(4-chlorophenyl)ethyl]-N-methylcyclopentane-1,2-diamine and the requisite carboxylic acid using General Procedure D.

Example 11

(±)-trans-1-{2-[2-(4-Chlorophenyl)ethylamino]cyclopentyl}-3-(3,4,5-trimethoxyphenyl)urea hydrochloride; MS m/z 448 (+1)$^+$.

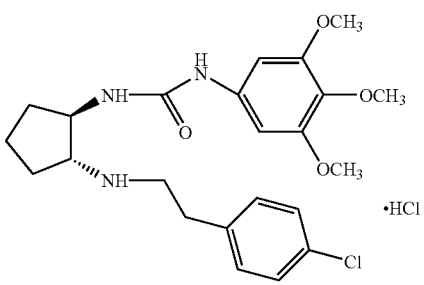

Using the procedure described in Example 1, the title compound was prepared from (±)-trans-[2-(4-chlorophenyl)ethyl]-{2-[3-(3,4,5-trimethoxyphenyl)ureido]cyclopentyl}carbamic acid tert-butyl ester.

The intermediate (±)-trans-[2-(4-chlorophenyl)ethyl]-{2-[3-(3,4,5-trimethoxyphenyl)ureido]cyclopentyl}carbamic acid tert-butyl ester was prepared as described in Example 3, by replacing the (±)-trans-(2-aminocyclopentyl)-[3-(4-chlorophenyl)propyl]carbamic acid tert-butyl ester used therein with (±)-trans-(2-aminocyclopentyl)-[2-(4-chlorophenyl)ethyl]carbamic acid tert-butyl ester.

Example 12

(±)-trans-N-{2-[2-(4-Chlorophenyl)ethylamino]cyclopentyl}-2-[5-(3,4-dimethoxyphenyl)pyrimidin-2-ylsulfanyl]acetamide hydrochloride

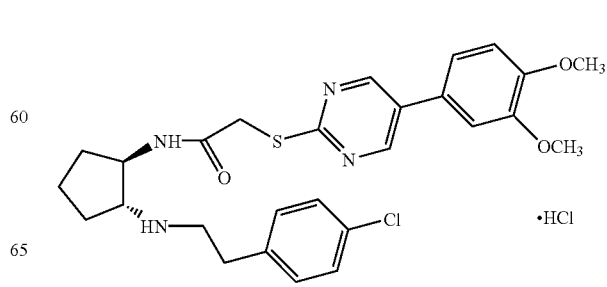

Using the procedure described in Example 1, the title compound was prepared from (±)-trans-[2-(4-chlorophenyl)ethyl]-(2-{2-[5-(3,4-dimethoxy-phenyl)pyrimidin-2-ylsulfanyl]acetylamino}cyclopentyl)carbamic acid tert-butyl ester; MS m/z 527 (M+1)+.

The intermediate (±)-trans-[2-(4-chlorophenyl)ethyl]-(2-{2-[5-(3,4-dimethoxyphenyl)pyrimidin-2-ylsulfanyl]acetylamino}cyclopentyl)carbamic acid tert-butyl ester was prepared as described in Example 1, by replacing the 3-(4-chlorophenyl)propylamine used in Step B with 2-(4-chlorophenyl)ethylamine.

Example 13

Formulation Examples

The following are representative pharmaceutical Formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbit (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable Formulation.

| Ingredient | Amount |
|---|---|
| compound of this invention | 0.2 g |
| sodium acetate buffer solution, | 0.4 M 2.0 ml |
| HCl (1N) or NaOH (1N) | q.s. to suitable pH |
| water (distilled, sterile) | q.s. to 20 ml |

Liposomal Formulation

The following ingredients are mixed to form a liposomal Formulation.

| Ingredient | Amount |
|---|---|
| compound of this invention | 10 mg |
| L-.alpha.-phosphatidylcholine | 150 mg |
| tert-butanol | 4 ml |

Freeze dry the sample and lypholize overnight. Reconstitute the sample with 1 ml 0.9% saline solution. Liposome size can be reduced by sonication Example 14

CCR-3 Receptor Binding Assay—In Vitro

The CCR-3 antagonistic activity of the compounds of the invention was determined by their ability to inhibit the binding of $^{125}$I eotaxin to CCR-3 L1.2 transfectant cells (see Ponath, P. D. et al., J. Exp. Med., Vol. 183, 2437–2448, (1996)).

The assay was performed in Costar 96-well polypropylene round bottom plates. Test compounds were dissolved in DMSO and then diluted with binding buffer (50 mM HEPES, 1 mM CaCl.sub.2, 5 mM MgCl$_2$, 0.5% bovine serum albumin (BSA), 0.02% sodium azide, pH 7.24) such that the final DMSO concentration was 2%. 25 µl of the test solution or only buffer with DMSO (control samples) was added to each well, followed by the addition of 25 µl of $^{125}$I-eotaxin (100 pmol) (NEX314, New England Nuclear, Boston, Mass.) and 1.5×10$^5$ of the CCR-3 L1.2 transfected cells in 25 µl binding buffer. The final reaction volume was 75 µl.

After incubating the reaction mixture for 1 hour at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 minutes. 25 µl/well of Microscint-20® scintillation fluid (Packard) was added and the radioactivity retained on the filters was determined by using the Packard TopCount®

Compounds of this invention were active in this assay. Representative data are shown below.

| Compound Number from Table 1 | IC50 (µM) |
|---|---|
| 1 | 18.2 |
| 2 | 6.8 |
| 6 | 5.4 |
| 9 | 5.6 |

Example 15

Inhibition of Eotaxin Mediated Chemotaxis of CCR-3 L1.2 Transfectant Cells—In Vitro Assay The CCR-3 antagonistic activity of the compounds of this invention can be determined by measuring the inhibition of eotaxin mediated chemotaxis of the CCR-3 L1.2 transfectant cells, using a slight modification of the method described in Ponath, P. D. et al., J. Clin. Invest. 97: 604–612 (1996). The assay is performed in a 24-well chemotaxis plate (Costar Corp., Cambridge, Mass.). CCR-3 L1.2 transfectant cells are grown in culture medium containing RPMI 1640, 10% Hyclone® fetal calf serum, 55 mM 2-mercaptoethanol and Geneticin 418 (0.8 mg/ml). 18–24 hours before the assay, the transfected cells are treated with n-butyric acid at a final concentration of 5 mM/$1\times10^6$ cells/ml, isolated and resuspended at $1\times10^7$ cells/ml in assay medium containing equal parts of RPMI 1640 and Medium 199 (M 199) with 0.5% bovine serum albumin.

Human eotaxin suspended in phosphate buffered saline at 1 mg/mil is added to bottom chamber in a final concentration of 100 nm. Transwell culture inserts (Costar Corp., Cambridge, Mass.) having 3 micron pore size are inserted into each well and L1.2 cells ($1\times10^6$) are added to the top chamber in a final volume of 100 μl. Test compounds in DMSO are added both to the top and bottom chambers such that the final DMSO volume is 0.5%. The assay is performed against two sets of controls. The positive control contained cells with no test compound in the top chamber and only eotaxin in the lower chamber. The negative control contains cells with no test compound in the top chamber and neither eotaxin nor test compound in lower chamber. The plate is incubated at 37° C. After 4 hours, the inserts are removed from the chambers and the cells that have migrated to the bottom chamber are counted by pipetting out 500 μl of the cell suspension from the lower chamber to 1.2 ml Cluster tubes (Costar) and counting them on a FACS for 30 seconds.

Example 16

Inhibition of Eotaxin Mediated Chemotaxis of Human Eosinophils—In Vitro Assay The ability of compounds of the invention to inhibit eotaxin mediated chemotaxis of human eosinophils can be assessed using a slight modification of procedure described in Carr, M. W. et al., Proc. Natl. Acad. Sci. USA, 91: 3652–3656 (1994). Experiments are performed using 24 well chemotaxis plates (Costar Corp., Cambridge, Mass.). Eosinophils are isolated from blood using the procedure described in PCT Application, Publication No. WO 96/22371. The endothelial cells used are the endothelial cell line ECV 304 obtained from European Collection of Animal Cell Cultures (Porton Down, Salisbury, U.K.). Endothelial cells are cultured on 6.5 mm diameter Biocoat.RTM. Transwell tissue culture inserts (Costar Corp., Cambridge, Mass.) with a 3.0 μM pore size. Culture media for ECV 304 cells consists of M199, 10% Fetal Calf Serum, L-glutamine and antibiotics. Assay media consists of equal parts RPMI 1640 and M199, with 0.5% BSA. 24 hours before the assay $2\times10^5$ ECV 304 cells are plated on each insert of the 24-well chemotaxis plate and incubated at 37° C. 20 nM of eotaxin diluted in assay medium is added to the bottom chamber. The final volume in bottom chamber is 600 μl. The endothelial coated tissue culture inserts are inserted into each well. $10^6$ eosinophil cells suspended in 100 μl assay buffer are added to the top chamber. Test compounds dissolved in DMSO are added to both top and bottom chambers such that the final DMSO volume in each well was 0.5%. The assay is performed against two sets of controls. The positive control contains cells in the top chamber and eotaxin in the lower chamber. The negative control contains cells in the top chamber and only assay buffer in the lower chamber. The plates are incubated at 37° C. in 5% $CO_2$/95% air for 1–1.5 hours.

The cells that migrate to the bottom chamber are counted using flow cytometry. 500 μl of the cell suspension from the lower chamber are placed in a tube, and relative cell counts are obtained by acquiring events for a set time period of 30 seconds.

Example 17

Inhibition of Eosinophil Influx Into the Lungs of Ovalbumin Sensitized Balb/c Mice by CCR-3 Antagonist—In Vivo Assay The ability of the compounds of the invention to inhibit leukocyte infiltration into the lungs can be determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25 g are sensitized with OA (10 μg in 0.2 ml aluminum hydroxide solution) intraperitoneally on days 1 and 14. After a week, the mice are divided into ten groups. Test compound or only vehicle (control group) or anti-eotaxin antibody (positive control group) is administered either intraperitoneally, subcutaneously or orally. After 1 hour, the mice are placed in a Plexiglass box and exposed to OA aerosol generated by a PARISTAR.TM. nebulizer (PARI, Richmond, Va.) for 20 minutes. Mice which have not been sensitized or challenged are included as a negative control. After 24 or 72 hours, the mice are anesthetized (urethane, approx. 1 g/kg, i.p.), a tracheal cannula (PE 60 tubing) is inserted and the lungs are lavaged four times with 0.3 ml PBS. The BAL fluid is transferred into plastic tubes and kept on ice. Total leukocytes in a 20 μl aliquot of the BAL fluid is determined by Coulter Counter.™. (Coulter, Miami, Fla.). Differential leukocyte counts are made on Cytospin.™. preparations which have been stained with a modified Wright's stain (DiffQuick.™.) by light microscopy using standard morphological criteria.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

I claim:
1. A compound of Formula (I):

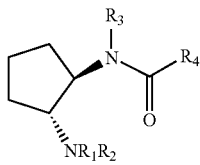

wherein:
$R_1$ is hydrogen or alkyl;
$R_2$ is arylalkyl;
$R_3$ is hydrogen, alkyl, acyl, aryl, or arylalkyl;
$R_4$ is —W—X—Y—Z;
W is alkylene;
X is —S(O)$_n$—;
Y is heteroarylene; and
Z is aryl;
$R_a$ is hydrogen, alkyl, acyl, aryl, arylalkyl, alkoxycarbonyl, or benzyloxycarbonyl; and
each n is 0;
or a pharmaceutically acceptable salt thereof.

2. The compound of claim 1 wherein $R_1$ is hydrogen.

3. The compound of claim 2 wherein $R_2$ is phenylalkyl, wherein the phenyl is optionally substituted with one, two or three substituents independently selected from the group consisting of alkyl, halo, cyano, nitro, alkoxy, haloalkoxy, hydroxy, amino, acylamino, alkylamino, and dialkylamino.

4. The compound of claim 3 wherein $R_2$ is phenylalkyl, wherein the phenyl is substituted with one, two or three halo substituents.

5. The compound of claim 4 wherein $R_2$ is phenylalkyl, wherein the phenyl is substituted with one halo substituent.

6. The compound of claim 5 wherein $R_2$ is (4-chlorophenyl)alkyl.

7. The compound of claim 6 wherein $R_2$ is 2-(4-chlorophenyl)ethyl, or 3-(4-chlorophenyl)propyl.

8. The compound of claim 1 wherein $R_3$ is hydrogen or methyl.

9. The compound of claim 1, wherein Y—Z is 5-arylpyrimidin-2-yl.

10. The compound of claim 1 wherein —Y—Z is 5-(3,4-dimethoxyphenyl)pyrimidin-2-yl.

11. The compound of claim 1 wherein Y—Z is 5-arylpyrimidin-2-yl.

12. The compound (±)-trans-N- {2-[3-(4-chlorophenyl)propylamino]-cyclopentyl}-2-[5-(3,4-dimethoxyphenyl)pyrimidin-2-ylsulfanyl]acetamide;

(±)-trans-N-(2-{[3-(4-chlorophenyl)propyl]methylamino}-cyclopentyl)-2-[5-(3,4-dimethoxyphenyl)pyrimidin-2-ylsulfanyl]acetamide;

(±)-trans-N-(2-{[2-(4-chlorophenyl)ethyl]methylamino}-cyclopentyl)-2-[5-(3,4-dimethoxyphenyl)pyrimidin-2-ylsulfanyl]acetamide;

(±)-Trans-N-{2-[2-(4-chlorophenyl)ethylamino]cyclopentyl}-2-[5-(3,4-dimethoxy-phenyl)pyrimidin-2-ylsulfanyl]-acetamide; or a pharmaceutically acceptable salt thereof.

13. A composition containing a therapeutically effective amount of a compound of Formula (I) as described in claim 1, or a salt thereof; and an excipient.

* * * * *